(12) United States Patent
Gallen et al.

(10) Patent No.: US 9,171,216 B2
(45) Date of Patent: Oct. 27, 2015

(54) METHOD AND DEVICE FOR DETECTING FOG AT NIGHT

(75) Inventors: Romain Gallen, Paris (FR); Aurélien Cord, Paris (FR); Nicolas Hautiere, Paris (FR); Didier Aubert, Mennecy (FR)

(73) Assignee: INSTITUT FRANCAIS DES SCIENCES ET TECHNOLOGIES DES TRANSPORTS, DE L'AMENAGEMENT ET DES RESEAUX, Champs sur Marne (FR)

( * ) Notice: Subject to any disclaimer, the term of this patent is extended or adjusted under 35 U.S.C. 154(b) by 228 days.

(21) Appl. No.: 13/876,138

(22) PCT Filed: Sep. 28, 2011

(86) PCT No.: PCT/FR2011/052262
§ 371 (c)(1),
(2), (4) Date: Oct. 18, 2013

(87) PCT Pub. No.: WO2012/042171
PCT Pub. Date: Apr. 5, 2012

(65) Prior Publication Data
US 2014/0029790 A1    Jan. 30, 2014

(30) Foreign Application Priority Data
Sep. 28, 2010  (FR) ...................................... 10 57802

(51) Int. Cl.
*G06K 9/00*   (2006.01)
*G01N 21/53*  (2006.01)
*G01W 1/00*   (2006.01)
*G01N 21/47*  (2006.01)

(52) U.S. Cl.
CPC .......... *G06K 9/00805* (2013.01); *G01N 21/538* (2013.01); *G01W 1/00* (2013.01); *G06K 9/00825* (2013.01); *B60Q 2300/312* (2013.01); *G01N 2021/4709* (2013.01)

(58) Field of Classification Search
None
See application file for complete search history.

(56) References Cited

U.S. PATENT DOCUMENTS

| 6,853,453 | B2  |   | 2/2005 | Kwon |
| 7,423,752 | B2  |   | 9/2008 | Leleve et al. |
| 8,023,760 | B1  | * | 9/2011 | Buck et al. ..................... 382/260 |
| 2002/0040962 | A1 |   | 4/2002 | Schofiled et al. |
| 2008/0007429 | A1 |   | 1/2008 | Kawasaki et al. |
| 2010/0124274 | A1 | * | 5/2010 | Cheok et al. ............. 375/240.03 |
| 2010/0172542 | A1 | * | 7/2010 | Stein et al. .................... 382/103 |

FOREIGN PATENT DOCUMENTS

| EP | 1715456  | 10/2006 |
| EP | 2172873  | 4/2010 |
| JP | 11-278182 | 10/1999 |

* cited by examiner

*Primary Examiner* — Siamak Harandi
(74) *Attorney, Agent, or Firm* — Hamre, Schumann, Mueller & Larson, P.C.

(57) ABSTRACT

A method of detecting the presence of an element (fog, rain, etc. . . . ) disturbing the visibility of a scene illuminated by a headlight (105, 107) at night. The method comprises:
 a) acquiring an image of the scene with the help of a camera (120);
 b1) detecting the light sources in the image;
 b2) detecting the presence of the disturbing element as a function of the halo (H) appearing in the image in the vicinity of the light sources;
 c) detecting the presence of the disturbing element in the image as a function of the backscattering of the light emitted by the light sources; and
 d) weighting the results of the detections performed in steps b2) and c) in such a manner as to output an indication concerning the presence of the element disturbing the visibility of the scene.

The method provides satisfactory results in an environment with or without lighting. The invention also provides a computer program and a device for implementing the method.

15 Claims, 5 Drawing Sheets

METHOD AND DEVICE FOR DETECTING FOG AT NIGHT

FIELD

The invention relates to a method for use at night for detecting the presence of an element such as fog disturbing the visibility of a scene, the scene being illuminated by one or more light sources.

The invention relates in particular to detecting such a disturbing element when the scene is that which appears in the field of view of a driver of a vehicle, in particular a road vehicle; by detecting such an element, the invention helps in determining the driver's visibility distance, and enables the driving and the behavior of the vehicle to be adapted to visibility conditions, optionally in automatic manner. The invention also provides a computer program enabling the method to be performed, a device for performing the method, and finally a vehicle including such a device.

BACKGROUND

The invention thus finds applications in the automotive field, and in particular in the field of road vehicle lighting and signaling, and also in the field of video surveillance.

There already exist devices that enable the presence of fog to be detected. Such devices are used in particular for automatically causing lights and lighting devices to be switched on and for enabling drivers to adapt the speed of their vehicles as a function of the visibility of the road scene situated in front of their vehicles.

One such device for detecting the presence of fog makes use of an anticollision device of the light detection and ranging (LIDAR) type that serves to evaluate transmission through the atmosphere in order to deduce the presence of fog. Unfortunately, LIDARs are devices that are very expensive; it is therefore difficult to envisage installing them systematically on transport vehicles.

Another device, as proposed in document U.S. Pat. No. 6,853,453, makes use of targets arranged in the scene under study in order to detect the presence of a disturbing element. That method requires targets to be placed in the scene, which is very constricting, and impossible for mobile applications.

Another device, proposed by document JP 11-278182, is based on identifying and characterizing the light halo that appears around the taillights of a vehicle that appears in the scene being studied. The drawback of that system is that it does not operate when there is no vehicle light that appears in the scene.

Another device, proposed by document US 2008/0007429, makes use of the backscattering of the light from the headlights of the vehicle in which the device is arranged. Nevertheless, that system is not sufficiently reliable, in particular because it is based on very local analysis of the image and it is found to be ineffective for detecting the presence of an element disturbing the visibility in certain environments, in particular in environments that are fairly well lit.

It can thus be understood that a relatively large number of devices have been proposed for detecting fog at night. Nevertheless, none of those devices is genuinely satisfactory. Each of those devices is effective only in a limited operating range, and is found to be incapable of detecting fog effectively under other atmospheric conditions.

BRIEF SUMMARY

The object of the invention is thus to remedy the shortcomings of those various devices, and to propose a method of detecting the presence of an element disturbing the visibility of a scene illuminated by at least one light source at night; said element belonging to the group comprising fog, smoke, rain, and snow; the method comprising a step a) in which at least one image of the scene is acquired with the help of a camera, said at least one light source being stationary or swivel-mounted relative to the camera; which method provides a result that is satisfactory under most circumstances, and does not require specific elements to be present or to put into place in the scene.

This object is achieved by the fact that the method further comprises the following steps:

b1) detecting at least one light source forming part of the scene in said at least one image;

b2) detecting the presence of a disturbing element as a function of the halo appearing in said at least one image in the vicinity of said light source(s);

c) detecting the presence of a disturbing element in said at least one image or in a portion thereof as a function of the backscattering of light emitted by said stationary or swivel-mounted light source(s); and d) weighting the results of the detections performed in steps b2) and c), in such a manner as to output an indication concerning the presence of an element disturbing the visibility of the scene.

It has been found that the effectiveness of the image analysis method usually performed in such devices depends strongly on the presence of light sources in the scene.

Advantageously, the method combines two complementary techniques for detecting the presence of a disturbing element:

steps b1) and b2): detecting a halo around a light source that has been identified in the scene; and step c): analyzing the backscattering of light emitted by the stationary or swivel-mounted light sources.

The advantage of combining those two techniques is as follows:

In an illuminated environment, techniques based on analyzing backscattering operate very poorly, since the intensity of the backscattered lighting is low and therefore difficult to identify among the various kinds of radiation being reflected towards the camera lens. Conversely, a lighted environment (typically an urban environment) includes light sources; and in the presence of light sources, halo analysis techniques are effective.

In an environment that is not lighted, the image of the scene depends to a great extent on the way in which the scene is illuminated by the stationary or swivel-mounted light source(s). By making use of the properties known in advance of the light beam produced by the stationary or swivel-mounted light source(s), it is possible to make effective use of the technique of analyzing the backscattering of the emitted light in order to detect the presence of the disturbing element.

It should be observed that the light source identified during step b1) is an active component that does indeed emit light, in general from a source of electricity, and not one that does no more than re-emitting radiation received from elsewhere. It is therefore not a passive component serving only to reflect and/or diffuse the light it receives, where such a component would usually be difficult to distinguish at night.

Advantageously, each of the steps b1), b2), and c) can be performed using a single image, or possibly a few successive images that have been smoothed, which images should be acquired sufficiently quickly to represent substantially the same view of the scene under study (possibly after a small amount of computer repositioning). Thus, the processing constituted by above-mentioned steps b1), b2), and c) only requires one substantially instantaneous acquisition. Furthermore, the information about the presence of a disturbing element can advantageously be obtained very quickly, e.g. as soon as the vehicle penetrates into a fog bank, which is very advantageous from a point of view of driving safety.

Furthermore, the steps b1), b2, and c) may be performed equally well with a monochrome camera or with a color camera, with color information being used only optionally for performing the invention.

The indication provided by the device of the invention about the presence of a disturbing element may be binary or many-valued, for example a percentage lying in the range 0% to 100%.

In the applications envisaged for the invention, the light source that illuminates the scene under study is usually stationary relative to the camera. Thus, for a device that is mounted on board a vehicle, the light source and the camera are both stationary relative to the vehicle. The light source is then typically a vehicle headlight and in particular, very often, the focus of the light source (the portion from which the radiation is emitted) does not appear in the camera image. With a device that is stationary, i.e. stationary relative to the ground, the light source may be any light source that is stationary relative to the ground, e.g. a street lamp or some other light.

An alternative solution is for the light source to be swivel-mounted or steerable relative to the camera. Thus, for example when the device is mounted on board a vehicle, swivel-mounted light sources may be steerable headlights of the vehicle.

The method may also advantageously present one or more of the following steps:

in step a), a plurality of images may be acquired, with the image of the scene being the mean of said plurality of images.

Step b2) is preferably a step during which the decrease of light intensity in a halo is characterized for the various halos being studied. Step b2) may include the following intermediate step:

b21) segmenting the image portions corresponding to light sources detected in step b1) in such a manner as to identify the light sources one by one and not grouped together.

Step b2) may include the following intermediate step:

for at least one image portion associated with an identified light source in the scene, detecting the presence of a disturbing element by identifying the center of the light source in said image portion.

Step b2) may include the following intermediate step:

b23) for at least one image portion associated with a light source identified in the scene, detecting the presence of a disturbing element by analyzing an intensity profile along a segment drawn in said at least one image portion.

This segment (analysis segment) may be determined by interpolating centers of the light source as calculated for different values for the threshold for extracting the halo surrounding the light source.

Step c) may include the following intermediate step:

c1) providing at least one reference image, either produced by a camera or else resulting from an optical simulation calculation.

Step c) may include the following intermediate step:

c2) comparing that said at least one image or said portion thereof with said at least one reference image in such a manner as to obtain a comparison score.

A second object of the invention is to propose a computer program including instructions for performing a method of detecting the presence of an element disturbing the visibility of a scene illuminated by at least one light source, at night; said element belonging to the group comprising: fog, smoke, rain, and snow; which program provides a satisfactory result in most circumstances when it is performed by a computer and does not require specific elements to be present in the scene or to be placed in the scene.

This object is achieved by the fact that the program includes instructions for performing a method as described above. The term "computer" includes any type of computer or calculation means, in particular on-board computers on vehicle.

The invention also provides a computer readable recording medium having a computer program as defined above recorded thereon.

A third object of the invention is to provide a device detecting the presence of an element disturbing the visibility of a scene illuminated by at least one light source, at night; said element belonging to the group comprising fog, smoke, rain, and snow; the device comprising a camera suitable for acquiring at least one image of the scene, and calculation means suitable for executing a program for processing images delivered by the camera; said at least one light source being a light source that is stationary or swivel-mounted relative to the camera; which device provides a result that is stationary under most circumstances, and does not require specific elements to be present in the scene or to be placed in the scene.

This object is achieved by the fact that in the device, the calculation means are suitable for executing the program for processing images delivered by the camera so as to execute the following operations:

b1) from said at least one image, detecting at least one light source that appears in the scene;

b2) detecting the presence of a disturbing element as a function of the halo appearing in said at least one image in the vicinity of said at least one light source;

c) detecting the presence of a disturbing element in said at least one image or in a portion thereof as a function of the backscattering of the light emitted by said on-board light source(s);

d) weighting the results of detections performed in steps b2) and c1), in such a manner as to output an indication concerning the presence of an element disturbing the visibility of the scene.

The device may also advantageously present one or more of the following improvements:

The processing program may be suitable for performing the following operations:

for at least one image portion associated with an identified light source in the scene, detecting the presence of a disturbing element by analyzing an intensity profile along a segment drawn in said at least one image portion. In particular, this segment may be determined by interpolating centers of the light source as calculated for different values of the threshold for extracting the halo surrounding the light source.

The calculation means may be suitable for executing the processing program in such a manner as to execute the following operation:

c2) comparing said at least one image or said portion thereof with said at least one reference image in such a manner as to obtain a comparison score.

The invention also provides a device for detecting the presence of an element disturbing the visibility of a scene illuminated by at least one light source, at night; said element belonging to the group comprising fog, smoke, rain, and snow: the device comprising:

a) a camera suitable for acquiring at least one image of the scene, said at least one light source being a light source that is stationary or swivel-mounted relative to the camera;

b1) means for detecting at least one light source belonging to the scene in said at least one image;

b2) means for detecting the presence of a disturbing element as a function of the halo appearing in said at least one image in the vicinity of said at least one light source;

c) means for detecting the presence of a disturbing element in said at least one image or in a portion thereof as a function of the backscattering of the light emitted by said on-board light source(s); and d) means for weighting the results of the detections performed in steps b2) and c1), in such a manner as to output an indication concerning the presence of an element disturbing the visibility of the scene.

It can be understood that together the above-described steps of calculation and in particular of detection can be performed by means of a computer program executed by a computer, and/or by electronic components designed for and capable of performing the same operations, by acting on electronic signals.

Finally, the invention provides a vehicle, in particular a road vehicle, in which driving is to be made safer because it is suitable for detecting the presence of an element disturbing visibility at night in a scene illuminated by at least one light source on board the vehicle; said disturbing element forming part of the group comprising fog, smoke, rain, and snow.

Such a vehicle is characterized by the fact that it incorporates a device as described above.

For the purposes of simplification, in the document below, the term "fog" is used to refer to the disturbing element, it being understood that the disturbing element could equally well be rain, snow, smoke, etc.

BRIEF DESCRIPTION OF THE DRAWINGS

The invention can be better understood and its advantages appear better on reading the following detailed description of embodiments given as nonlimiting examples. The description refers to the accompanying drawings, in which.

DETAILED DESCRIPTION

Figure 1:
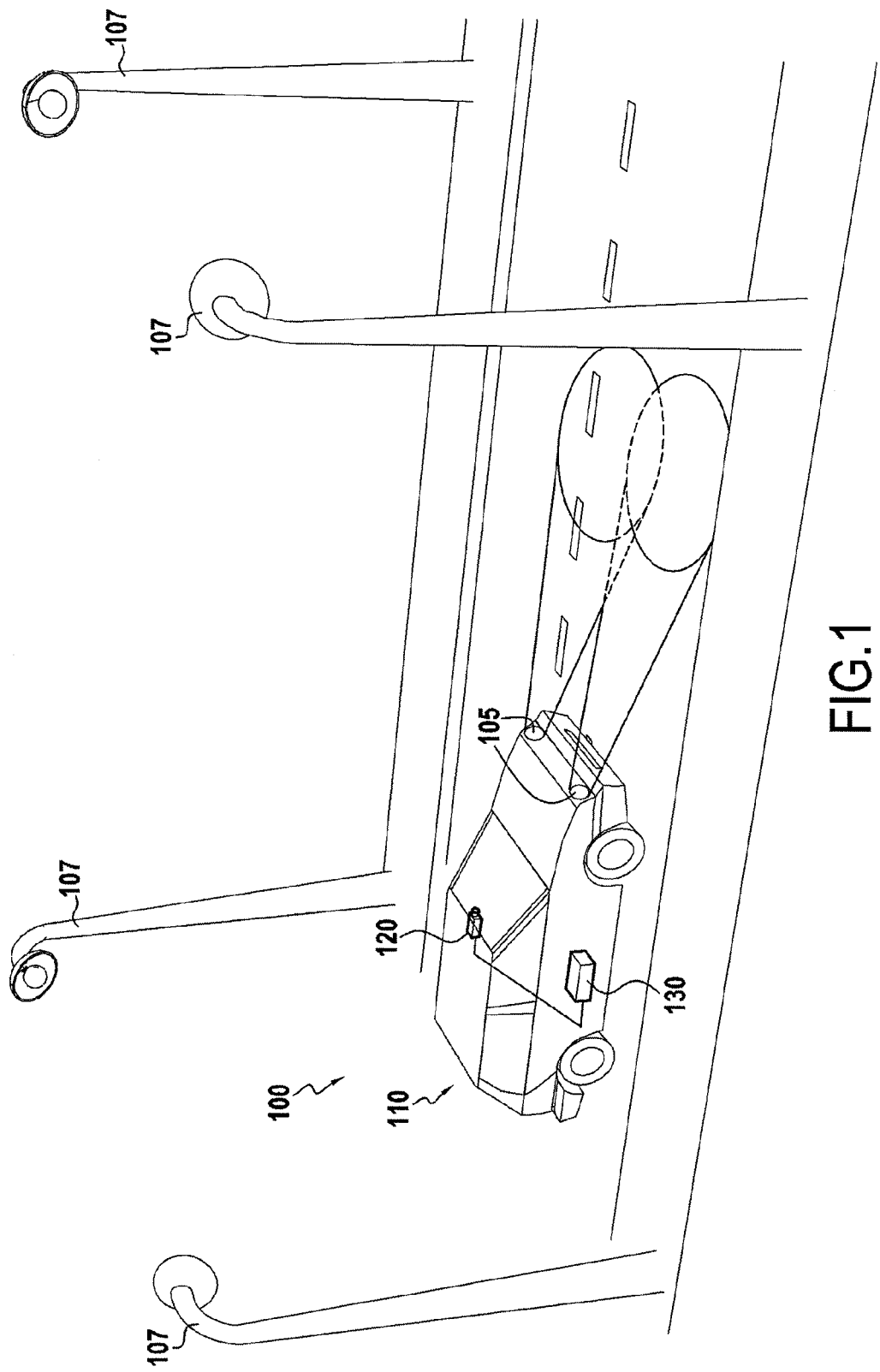
FIG. 1 is a diagrammatic view of a road vehicle including a device of the invention.

FIG. 1 shows a vehicle 100 including a fog detection device 110 of the invention. The vehicle has headlights 105 as on-board light sources. When these headlights are on, they illuminate the road in front of the vehicle. The road is also illuminated by other light sources, specifically street lamps 107.

The device 110 comprises an on-board camera 120 and an on-board computer 130. The computer is designed to execute a fog detection program on the basis of images delivered by the camera 120, when driving at night. The computer 130 has a read-only memory (ROM) that constitutes a recording medium in the meaning of the invention, and in which there is recorded a program in the meaning of the invention. The information obtained about the presence of fog is transmitted to the driver, and/or is used by the on-board computer 130 in order to control other equipment of the vehicle 100.

Figure 2:
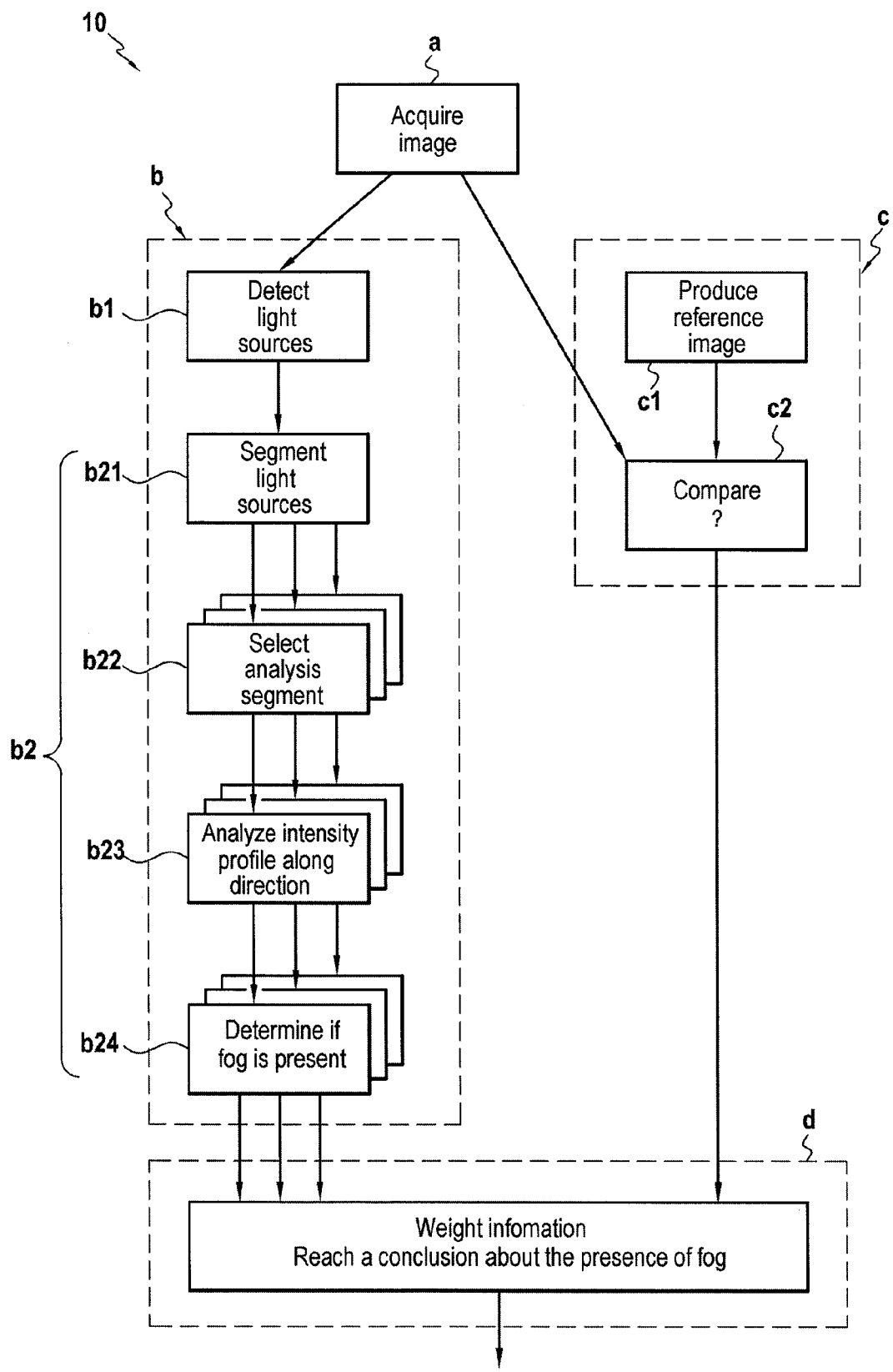
FIG. 2 is a flowchart showing the steps of a method of the invention in a particular implementation.

The method performed by the on-board computer 130 under the control of a computer program includes three stages (FIG. 2).

In a first stage a), one or more images of the scene are acquired using the camera. Generally, one image suffices. Nevertheless, in order to reduce noise, it is possible to average a plurality of images in order to produce one image. A single image is thus obtained (initial image).

Starting with the image or the images acquired during the step a), two processes are executed in parallel during a second stage.

The first process b) is detecting the presence of fog by halo detection.

In a first step b1) of this first process, the light sources that are visible in the scene, i.e. that appear in the initial image, are detected. The pixels illuminated by the various light sources are identified and grouped into pixel groups referred to as "halos" that correspond to the various light sources. The pixels included in the light source halo(s) are identified by the fact that they present light intensity that is higher than that of their surroundings. Thus, by means of a thresholding operation applied to the initial image, the various halos that appear in the image are identified and they are considered as representing the light sources that are visible in the scene. By way of example, it is possible to select an extraction threshold intensity lying in the range 80% to 99% of the maximum intensity that can be perceived by the camera. A halo may possibly encompass a plurality of light sources, if they are close together (in the image).

Figure 3A:
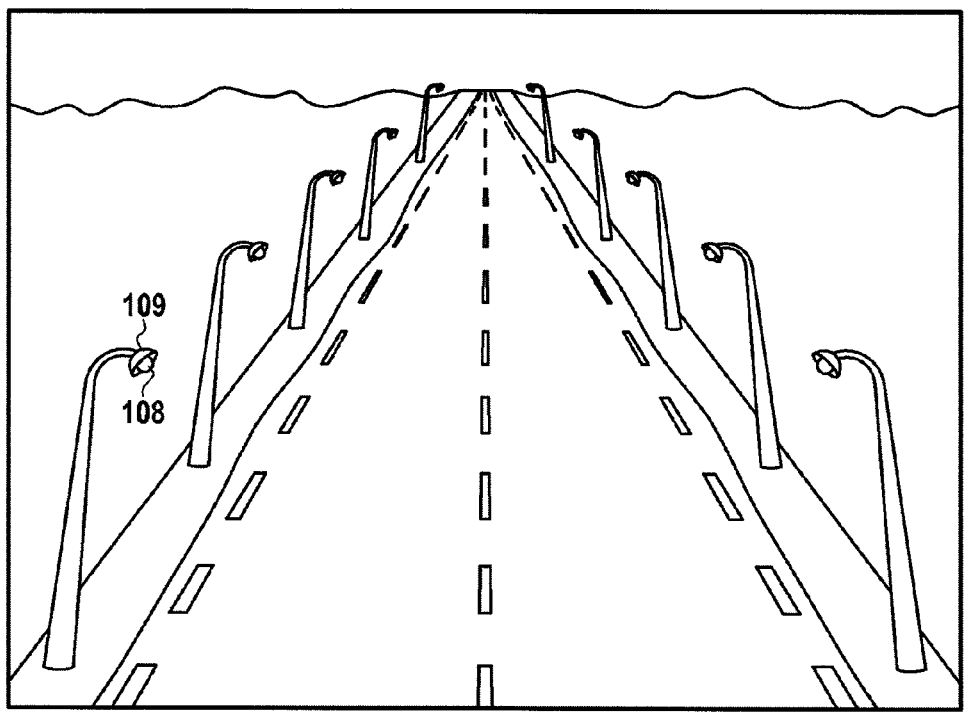
FIGS. 3A and 3B are simplified images of a night scene, respectively in dry weather and in foggy weather.
Figure 3B:
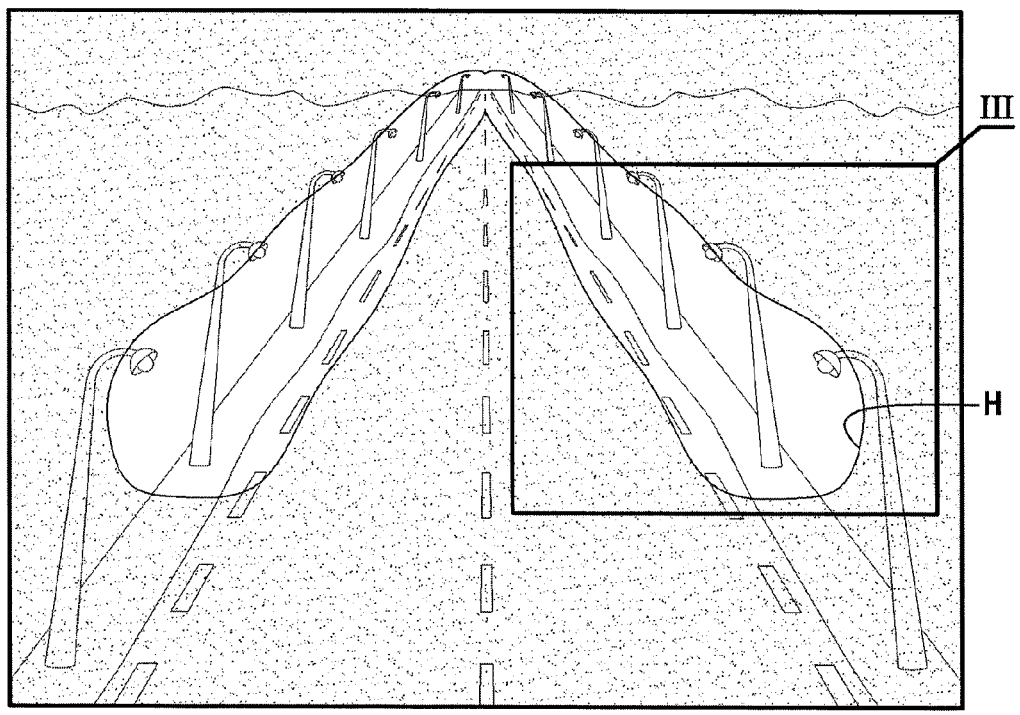

FIGS. 3A and 3B show the considerable differences that occur as a function of fog when detecting light sources in a given scene: FIG. 3A shows a scene without fog. Only the shining portion of each streetlight is identified (bulb 108 and cover 109). A halo (and thus a light source) is thus identified for each streetlight 107.

Conversely, FIG. 3B shows the same scene on a foggy night. The portions of the image that are illuminated by light from the streetlights merge and thus form only a single halo H extending along both sides of the road. The light source detection step thus begins by identifying only one light source.

After detecting light sources in the image, in a second step b2), and as a function of the halo(s) appearing in the image(s) in the vicinity of the light source(s), the presence of fog is detected. In other words, the halos identified in step b1) are analyzed; and by means of this analysis, the presence of fog is detected.

In the implementation described, this halo analysis step comprises a plurality of operations:

In a first operation b21), the light sources identified in step b1) are segmented so as to identify halos H1, H2, H3 each corresponding to a single light source instead of one halo H that actually corresponds to a set of light sources. In order to perform this segmentation, a plurality of thresholding operations are performed on the image while varying the value of the extraction threshold until the halos that correspond to distinct light sources become separated. For this operation, it is possible in particular to make use of algorithms for connected component analysis.

Figure 4A:
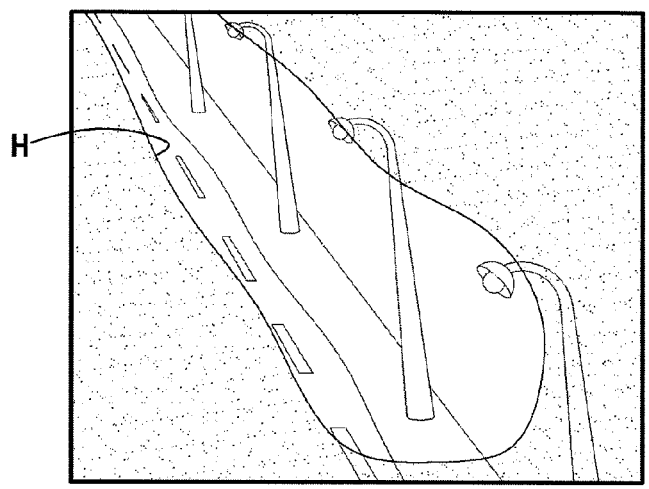
FIGS. 4A, 4B, and 4C show the same portion of the FIG. 3B image, but for different values of an extraction threshold used for extracting different zones corresponding to respective different light sources in this image portion.
Figure 4B:
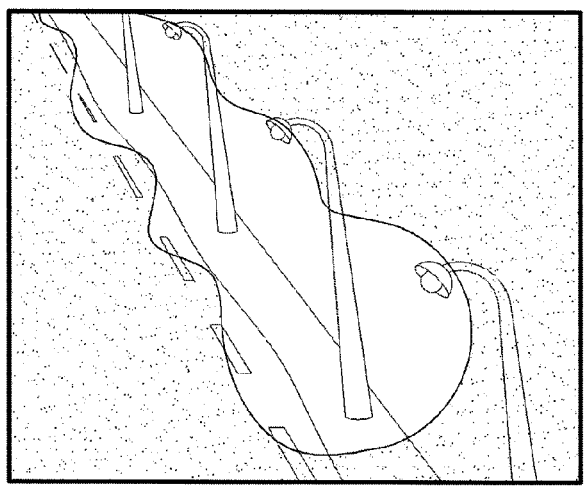
Figure 4C:

FIGS. 4A to 4C show the halos obtained with different values of the extraction threshold. FIG. 4A corresponds to a threshold that is quite low: the various light sources form a single halo H. FIG. 4B corresponds to an intermediate value. FIG. 4C corresponds to a threshold that is quite high, thereby enabling the initial halo to be segmented, and enabling halos H1, H2, and H3 to be distinguished within it, these halos corresponding to the three light sources that are indeed present in this portion of the image.

It should be observed that during the preceding operations (b1, b21), tests may be performed in order to eliminate erroneous detections of light sources in the scene. These tests may be based on the complexity of the identified halo (which complexity normally remains limited), on its size (eliminating the smallest light sources, which are assumed to be artifacts), etc.

Once the various light sources have been identified, the following operations are performed in parallel for each of the light sources:

In a second operation b22), an analysis segment is determined for each light source. The term "analysis segment" is used to mean a straight line segment under consideration in the image and along which an intensity profile analysis is performed. An analysis segment is determined by an iterative procedure. The proposed procedure begins on the basis of a tight halo H11 (FIG. 5A) as obtained with a very high intensity extraction threshold, i.e. a threshold that is very selective.

The following operations are then performed iteratively:
the center (C11, C12, C13 . . . ) of the halo is identified. Various calculations may be used for determining the center of a halo. For example, the center of the halo may be the center of gravity (i.e. the "barycenter") of the pixels of the light source; the center of gravity of the same pixels, but weighted by light intensity; the center of the ellipse that is the best approximation to the outline of the pixels of the light source; the center of the circle containing the pixels of the light source; etc.
the extraction threshold used for separating the pixels of the halo from the remainder of the image is lowered;
an extended halo (H12, H13 . . . ) is determined by recalculating using the new threshold value; and
it is verified whether the extended halo as recalculated in this way remains distinct from the halos of other light sources.

If it does not, the algorithm stops; otherwise the first step of the iterative procedure is repeated.

The iterative procedure thus provides a sequence of centers corresponding to the centers (C11, C12, C13 . . . ) of halos of ever-increasing extent. The sequence of centers as obtained in this way is then evaluated:

If a general direction appears, a straight line segment is drawn in the general direction of the sequence of centers, starting from the center corresponding to the smallest halo. Also, the analysis segment is oriented along the direction in which the center of the halo of the light source under consideration moves when the value of the halo extraction threshold is varied. It is calculated by interpolating from the positions of the centers C11, C12, C13 as determined, or by an analogous method. The analysis segment thus corresponds to the direction in which the halo extends, which direction generally corresponds to the lighting direction of the light source under consideration.

Figure 5A:
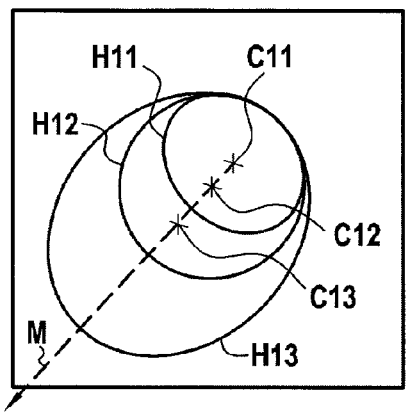
FIGS. 5A and 5B show an image portion in which there can be seen a light source respectively in foggy weather and in dry weather.

FIG. 5A thus shows an analysis segment M defined from the centers C11, C12, and C13 of the halos H11, H12, and H13 corresponding to three different values of the extraction threshold.

Figure 5B:
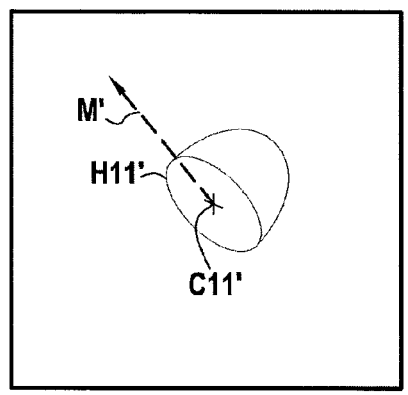

FIG. 5B shows a second analysis segment obtained for the same source, but in fog-free weather. Under such circumstances, even when varying the extraction threshold, only a single halo H11' can be extracted, corresponding to the zone that is made to shine directly by the bulb. Also, it is not possible to identify a preferred halo direction by interpolating the positions of the halo centers. Consequently, in order to obtain the analysis segment M', a direction is set arbitrarily. Care is taken to ensure that one end of the analysis segment M' used is the center C11' of the halo (and more generally under such circumstances, the end of the analysis segment may be the center of gravity (or barycenter) of the centers or it may be an analogous point).

The situation in which no preferred halo extension direction can be identified may correspond, for example, to the situation in which the light source is non-directional, as usually applies, for example, with the tail lights of a road vehicle. If no preferred direction appears, it is preferable to select an analysis segment having one end that is located towards the center and the top of the image, so that the end of the segment is likely to correspond to a region of sky, in the image under analysis.

In a third operation b23), for each light source, the variations in the lighting intensity profile along the analysis segment defined in step b22) are analyzed. Smoothing may optionally be performed on the curve of the intensity profile in order to reduce noise, e.g. by convolution using a smoothing window, by calculating the mean or median curve with the help of a window moving along the curve, etc.

The intensity profile variations are calculated for each of the light sources identified in the scene.

Thereafter, for each of the curves that is obtained, a fog-presence index is calculated. By way of non-exclusive example, this index may be based on: width at mid-height; width at various heights; the reciprocal of the slope at various heights; etc. It should be observed that for each of these indicators, the greater the value of the indicator, the greater the probability that fog is present.

Figure 6A:
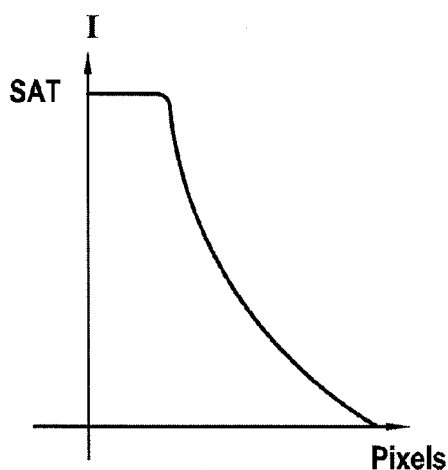
FIGS. 6A and 6B show curves for the variation in light intensity along segments that are shown in FIGS. 5A and 5B.
Figure 6B:
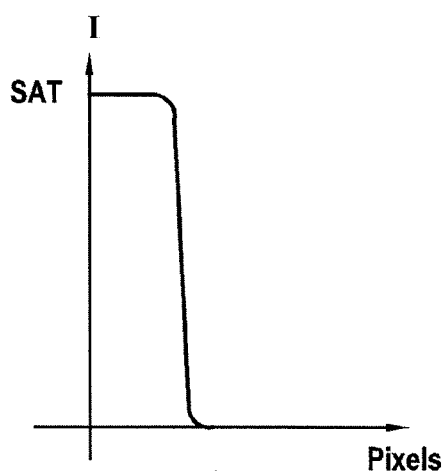

The curves in FIGS. 6A and 6B show the results obtained, respectively in foggy weather and in clear weather. Light intensity is plotted up the ordinate axis, and a distance expressed in pixels is plotted along the abscissa axis. These curves thus correspond to FIGS. 5A and 5B, respectively. Along segment M (FIGS. 5A, 6A), the light intensity curve comprises a first portion in the form of a plateau for which the pixels are saturated ('SAT'), followed by a slope descending progressively down to a value of zero intensity.

In contrast, along the segment M' (FIGS. 5B, 6B), the light intensity curve also has a first portion in the form of a plateau, but it has practically no progressive slope: the plateau is followed by a steep step in which the intensity drops suddenly. Using the various criteria mentioned above (width at mid-height or at several heights, etc), it is thus easy to see that the curves of FIGS. 6A and 6B provide results that are significantly different.

In a fourth operation b24), and overall fog-presence index is calculated. To do this, the various indices obtained for each of the light sources are aggregated. This aggregation or combination of indices serves to take account of indices coming not from a single initial image, but rather from a set of initial images acquired during step a). The aggregated index may for example be a mean or median value of the various fog-presence indices; it may be obtained by rank filtering, with various different levels; it may also be a linear combination with weighting based on a criterion, e.g. associated with the areas or the shapes of the halos of the light sources; etc.

Finally, the first processing for detecting the presence of fog by detecting halos may be concluded by a selection step, i.e. a step during which it is decided whether or not fog is present, in such a manner as to obtain a binary indicator. This decision is taken by comparing the overall fog-presence index with a predefined minimum threshold, associated with conventional thresholds, such as for example those recommended in French standard NF-P-99-320 on road weather.

The second processing c) of the second stage is processing for detecting the presence of fog by analyzing backscatter. This second processing relies on the principle that, in the presence of fog, a fraction of the radiation from the on-board light sources (specifically the vehicle headlights) is backscattered towards the camera.

Figure 7:
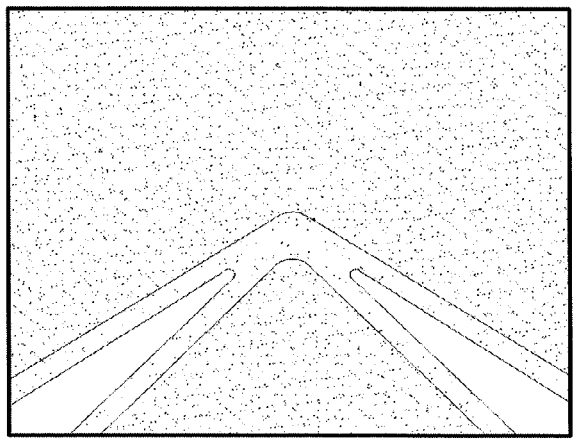
FIG. 7 is a reference image representative of the image that is obtained or that might be obtained in a non-illuminated environment, in foggy weather.

During a first step c1) of this second processing, one or more reference images of the scene are produced (FIG. 7). These images represent the scene as it might be observed in the event of fog. If the scene is stationary (as applies with video surveillance), the reference image(s) may include shapes coming from elements that are genuinely present in the scene. In contrast, if the scene is varying (as applies to a device on board a vehicle), the reference images are based solely on the backscattering of the light emitted by the on-board light sources.

FIG. 7 shows a reference image that can be used for a motor vehicle having two headlights. It is a grayscale image (or at least a monochrome image), showing only the variations in light intensity that are produced in the image by the two headlights beams. Arbitrary curves are shown in FIG. 7 to separate image portions of different luminosities. The curves appearing in FIG. 7 are thus iso-luminosity curves. These curves, and more generally the distribution of luminosity in the reference image, are characteristic of the lighting produced by the stationary or swivel-mounted light sources (the headlights of the vehicle), in association with defined fog conditions.

As a reference image, it is possible to use an image acquired by the camera, or a calculated synthetic image. With a synthetic image, any rendering method known to provide relatively realistic rendering of the scene may be used, providing it is capable of taking account of the backscattering of light in fog. The synthetic image must be calculated in such a manner as to represent as realistically as possible the image that the camera would acquire in the presence of fog. Naturally, the positions and lighting properties of the various light sources on board the vehicle and lighting the scene need to be taken into account.

Furthermore, several reference images may be used so as to represent the scene for different potential atmospheric conditions: not only fogs of greater or lesser density, but also conditions involving rain, snow, etc.

It may also be necessary to use a plurality of reference images when the light sources are swivel-mounted. The processing c) must be capable of being deformed regardless of the orientation of the light source(s). In order to achieve this objective, it is possible to use a library of reference images, corresponding respectively to the different possible orientations of the light source(s) (in discrete form).

The second and last step c2) of the second processing c) is a comparison step. The image or the images acquired by the camera is/are compared with the reference image(s) retained in step c1). Naturally, in order to reduce noise in the camera images and in order to simplify calculation, a plurality of images delivered by the camera may be aggregated so as to provide a single initial image, which image is then compared with the reference image(s). In this single initial image, each of the pixels may be calculated either as a mean of starting images, or else by means of a rank filter (e.g. a median filter) applied to a series of successive images, or by some other method of calculation.

The images coming from the camera and the reference images are compared with the help of image correlation methods. Various methods can be used. The comparison method may thus be based on the sum of absolute differences (SAD); on the zero mean sum of absolute differences (ZSAD), on the sum of squared differences (SSD), on the zero mean normalized sum of squared differences (ZNSSD), etc, or indeed on a method quantifying a difference between two images by a "distance" type function.

This comparison may be performed on the entire image, or on one or more image portions, e.g. the bottom half of the image (in which the illumination produced by the headlights is the most marked).

This comparison provides one or more indices for the presence of fog in the scene. An overall fog presence index can then be calculated by aggregating the various indices. In order to calculate this aggregate, in particular when the indices are obtained by comparing a single camera image with a plurality of reference images corresponding to different densities of fog, it is possible for example to select the presence index that has the highest value: it ought to correspond to the image that presents fog density that is close to the real fog density in the scene, at the instant of observation. This serves to characterize the fog.

The overall fog presence index, like the indices provided directly by the comparisons that are performed, has a value that increases with increasing probability of fog being present. If necessary, a binary indicator may then be established for whether or not fog is present (with/without fog), by comparing the overall index with a predetermined threshold.

The second stage of a method of the invention thus terminates by obtaining two families of indices for the presence of fog: indices calculated by the processing b) for halo detection, and the indices calculated by the processing c) for analyzing backscatter. Each family of these indices may be aggregated, or a single overall index may be derived therefrom. The index may optionally be binary.

Finally, in the final stage d) of the method, the fog presence indices are weighted with the help of a decision criterion, and a final index is calculated. By way of example, as a decision criterion, it is possible to select the number of light sources identified during step b21): if at least two sources are identified, then the overall index at the end of the processing b) is retained as indicating whether or not fog is present. If fewer than two sources are observed, then the index that is retained may be the overall index that results from the processing c). Naturally, other criteria may be retained while remaining within the ambit of the invention.

The invention claimed is:
1. A method of detecting the presence of an element disturbing the visibility of a scene illuminated by at least one light source at night; said element belonging to the group comprising fog, smoke, rain, and snow; the method comprising a step a) in which at least one image of the scene is acquired with the help of a camera, said at least one light source being stationary or swivel-mounted relative to the camera; the method further comprising the following steps:
   b1) detecting at least one light source forming part of the scene in said at least one image;

b2) detecting the presence of a disturbing element as a function of the halo appearing in said at least one image in the vicinity of said light source(s);

c) detecting the presence of a disturbing element in said at least one image or in a portion thereof as a function of the backscattering of light emitted by said stationary or swivel-mounted light source(s); and d) weighting the results of the detections performed in steps b2) and c), in such a manner as to output an indication concerning the presence of an element disturbing the visibility of the scene.

2. The method according to claim 1, wherein, in step a), a plurality of images are acquired, with the image of the scene being the mean of said plurality of images.

3. The method according to claim 1, wherein step b2) includes the following intermediate step:

b21) segmenting the image portions corresponding to light sources detected in step b1) in such a manner as to identify the light sources one by one and not grouped together.

4. The method according to claim 1, wherein step b2) includes the following intermediate step:

for at least one image portion associated with an identified light source in the scene, detecting the presence of a disturbing element by identifying the center of the light source in said image portion.

5. The method according to claim 1, wherein step b2) includes the following intermediate step:

b23) for at least one image portion associated with a light source identified in the scene, detecting the presence of a disturbing element by analyzing an intensity profile along a segment drawn in said at least one image portion.

6. The method according to claim 5, wherein said segment is determined by interpolating centers of the light source as calculated for different values for the threshold for extracting the halo surrounding the light source.

7. The method according to claim 1, wherein step c) includes the following intermediate step:

c1) providing at least one reference image, either produced by a camera or else resulting from an optical simulation calculation.

8. The method according to claim 7, wherein step c) includes the following intermediate step:

c2) comparing that said at least one image or said portion thereof with said at least one reference image in such a manner as to obtain a comparison score.

9. The method according to claim 8, wherein the comparison is performed by an image correlation method based on the sum of absolute differences, on the zero mean sum of absolute differences, on the sum of squared differences, on the zero mean normalized sum of squared differences, or indeed by a method quantifying a difference between two images by a function of the "distance" type.

10. A computer program stored on a non-transitory machine-readable medium, said computer program comprising instructions for performing the method according to claim 1 when executed by a computer.

11. A device detecting the presence of an element disturbing the visibility of a scene illuminated by at least one light source, at night; said element belonging to the group comprising fog, smoke, rain, and snow; the device comprising a camera suitable for acquiring at least one image of the scene, and one or more processors comprising calculation means suitable for executing a program for processing images delivered by the camera; said at least one light source being stationary or swivel-mounted relative to the camera; said calculation means being suitable for executing said program for processing images delivered by the camera in such a manner as to execute the following operations:

b1) from said at least one image, detecting at least one light source that appears in the scene;

b2) detecting the presence of a disturbing element as a function of the halo appearing in said at least one image in the vicinity of said at least one light source;

c) detecting the presence of a disturbing element in said at least one image or in a portion thereof as a function of the backscattering of the light emitted by said stationary or swivel-mounted light source(s);

d) weighting the results of detections performed in steps b2) and c1) in such a manner as to output an indication concerning the presence of an element disturbing the visibility of the scene.

12. The device according to claim 11, wherein said processing program is suitable for executing the following operations:

for at least one image portion associated with an identified light source in the scene, detecting the presence of a disturbing element by analyzing an intensity profile along a segment drawn in said at least one image portion.

13. The device according to claim 12, wherein said segment is determined by interpolating centers of the light source as calculated for different values of the threshold for extracting the halo surrounding the light source.

14. The device according to claim 11, wherein said processing program is suitable for executing the following operations:

c2) comparing said at least one image or said portion thereof with said at least one reference image in such a manner as to obtain a comparison score.

15. A vehicle, in particular a road vehicle, including the device according to claim 11.

* * * * *